United States Patent [19]
Anis

[11] Patent Number: 5,352,233
[45] Date of Patent: Oct. 4, 1994

[54] SCALPEL AND TECHNIQUE FOR USING SCALPEL

[76] Inventor: Aziz Y. Anis, 9540 Firethorne La., Lincoln, Nebr. 68520

[21] Appl. No.: 15,479

[22] Filed: Feb. 9, 1993

[51] Int. Cl.$^5$ .............................................. A61B 17/32
[52] U.S. Cl. .................................. 606/167; 606/166; 30/346
[58] Field of Search ....................... 606/166, 167, 101; 30/346, 289; 128/898

[56] References Cited

U.S. PATENT DOCUMENTS 3,840,015  10/1974  Gain ...................................... 606/167
5,201,747   4/1993  Mastel ................................... 606/167
5,217,476   6/1993  Wishinsky .

Primary Examiner—Stephen C. Pellegrino
Assistant Examiner—William Lewis
Attorney, Agent, or Firm—Vincent L. Carney

[57] ABSTRACT

To control the angle of an incision by a surgical scalpel during microsurgery, a scalpel has a double-beveled thin blade with reflective and light-absorbing matted portions on its surface whereby glare from the reflective portions of the blade indicates the angle of an incision. The matted portions are spaced longitudinally along the blade of the scalpel against a reflective background. A source of light in the microscope is reflected into the eye piece of the microscope from the blade so that the pattern of reflective and matted portions indicates the angle of the blade with respect to the light source.

11 Claims, 2 Drawing Sheets

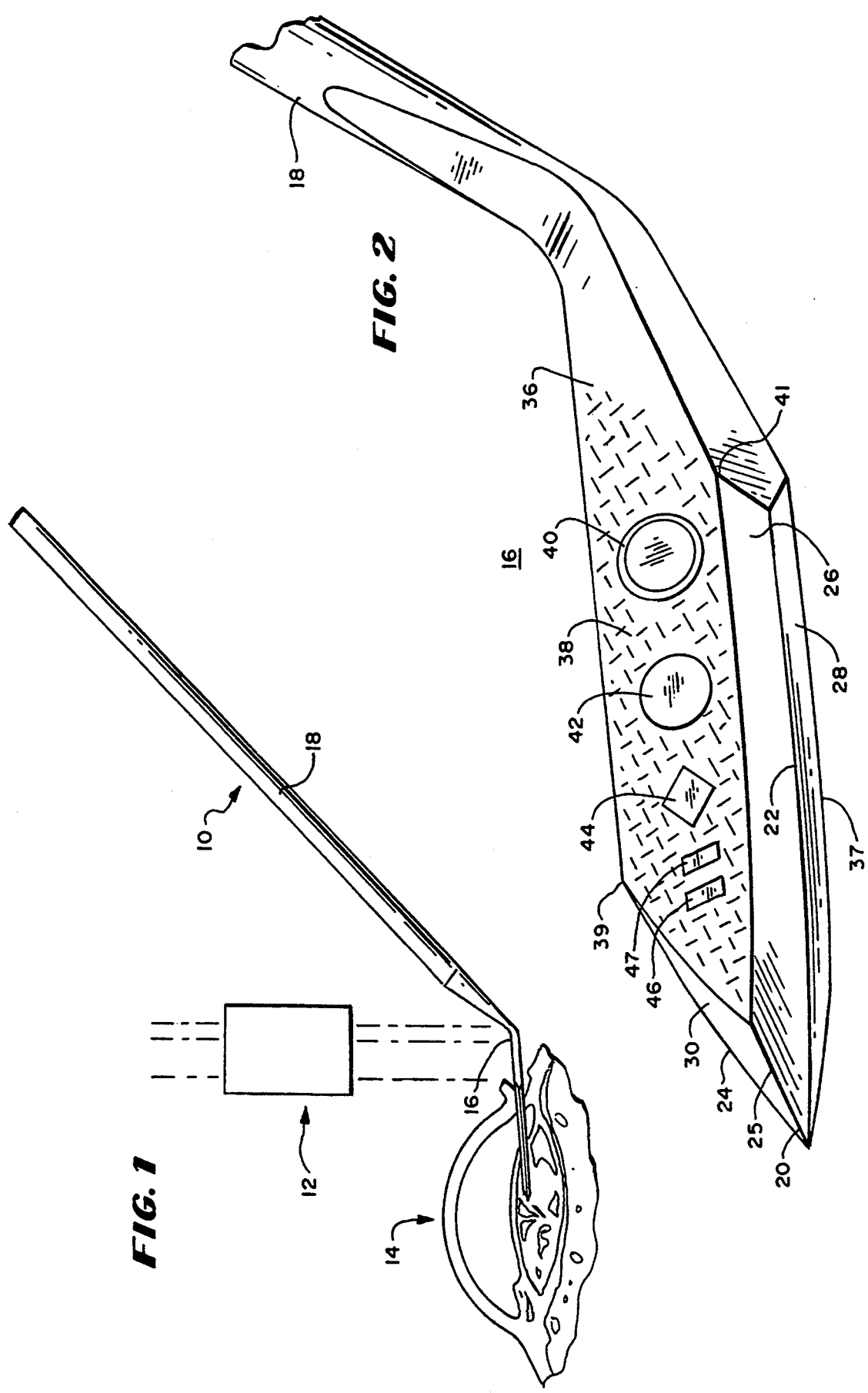

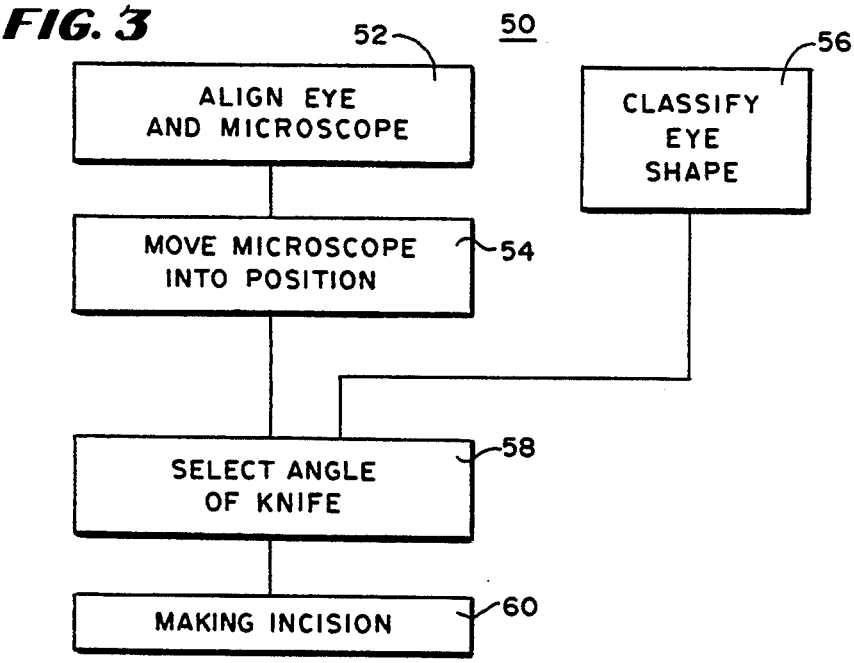
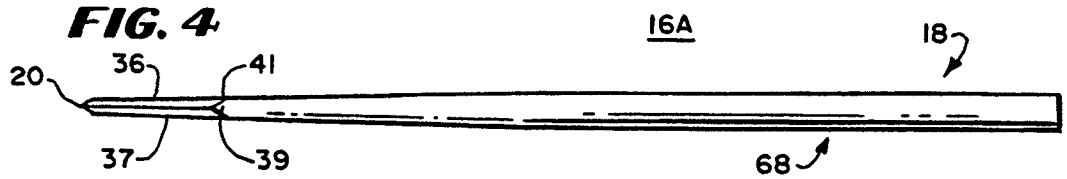
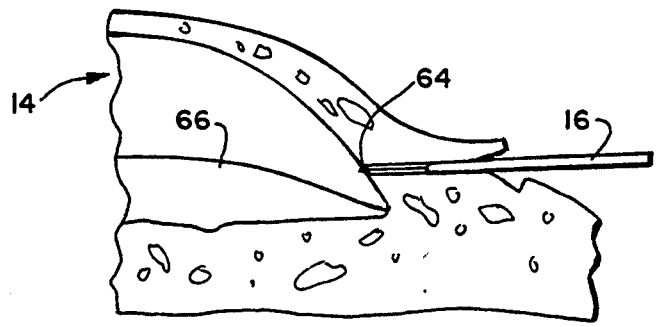
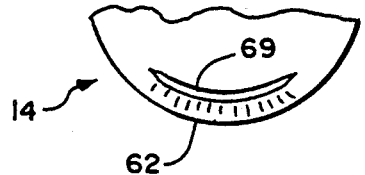

SCALPEL AND TECHNIQUE FOR USING SCALPEL

BACKGROUND OF THE INVENTION

This invention relates to a scalpel used in microsurgery and a technique for using the scalpel in such surgery.

One class of scalpel includes a thin blade having both of its flat sides beveled and tapered to a point to form substantially centered sharp edges, each of which is formed of bevels from the top and bottom of the blade.

One use of such scalpels is during microsurgery, such as surgery on the eye. The double beveled surfaces that form centered sharp edges make it easier for the surgeon to avoid unequal force exerted on each side of the blade by tissue as the incision is made. Otherwise, the unequal forces from tissue at the incision may cause the incision to be at an angle in a direction other than that which the surgeon plans because the unequal forces of tissue bearing against the blade change its orientation.

In one prior art scalpel of this class of scalpels, the surfaces are polished, stainless steel with high reflectivity. This type of surface has been criticized as creating undue glare for the surgeon since the light passing downwardly from the microscope is reflected directly up along the axis of the microscope when the knife is flat. This light causes undue glare.

Another prior art type of scalpel in this class has a matted surface designed to scatter light and thus reduce glare. However, the positioning of the blade continues to be a problem in some types of surgical procedures.

In one surgical procedure, a bent double-beveled surgical knife is used in connection with an incision, such as for example, to make sutureless incisions during cataract surgery. In making such an incision, the angle of the incision may result in an opening that is too small to accommodate the instruments or too large to close properly or shaped improperly so that it does not close properly or causes wrinkling of the cornea of the patient in a manner that impairs the ability of the surgeon to visualize the remainder of the operation through the cornea.

SUMMARY OF THE INVENTION

Accordingly, it is an object of the invention to provide a novel scalpel.

It is a further object of the invention to provide a novel technique using microsurgical scalpels.

It is a further object of the invention to provide a novel technique for controlling the angle of a scalpel blade during surgery.

It is a still further object of the invention to provide a novel technique for cataract surgery using a novel scalpel.

In accordance with the above and further objects of the invention, a scalpel blade has edges tapering to a point. The edges are formed of beveled surfaces from both sides of the blade so as to slope both from the top and bottom of the scalpel blade, joining each other at a sharp edge centered between the flat sides and having substantially equal length slopes forming equal angles with the center plane of the blade. All four beveled sides terminate at the distal point of the scalpel blade.

When using this scalpel, light reflected from the surface informs the surgeon about the angle of the blade, so that in making some incisions, the blade may be maintained level by reflecting light back into the microscope along the microscope axis during an incision. In such a case, the beveled edges on the two sides aid the surgeon in positioning the blade as the incision is made.

In a special surgical blade, the technique is further aided by indicia on a flat side of the blade that provides an indication of the angle of the blade even though the blade may not be held orthogonal to the axis of the microscope. This indicia may include spots or lines or geometric shapes or the like reflected from a more reflective portion of the blade so that as the blade assumes different angles, the surgeon views different reflections. The ability to reliably establish a selected angle for the incision is especially useful when making an incision in eyes having cornea and schlera which differ from the shape of the average eye.

In this technique, a corneal valvular or sutureless incision is made that is wide enough to effectively seal when the anterior chamber is pressurized but not so wide as to cause posterior pulling on the cornea at either extremity of the incision. The free edge of the internal corneal valve is smooth, regular and curvilinearly concentric with the limbus and just a short distance central of the central outline of the peripheral corneal capillary ring.

From the above description, it can be understood that the scalpel and the technique of using scalpels of this invention have several advantages, such as: (1) the double-beveled edges aid the surgeon in maintaining a preplanned course of the incision; (2) glare from a polished upper surface can be used in the technique of this invention to provide a proper sutureless incision; and (3) in one embodiment of the invention, a specially coded upper surface enables accurate control of the angle of the scalpel blade during an incision.

SUMMARY OF THE DRAWINGS

The above noted and other features of the invention will be better understood from the following detailed description when taken with reference to the accompanying drawings, in which:

FIG. 1 is a fragmentary, partly sectioned, partly schematic view illustrating the use of the scalpel in accordance with an embodiment of the invention;

FIG. 2 is a fragmentary perspective view of one embodiment of scalpel in accordance with the invention;

FIG. 3 is a block diagram depicting one embodiment of the technique in accordance with an embodiment of the invention;

FIG. 4 is a fragmentary side view of a blade in accordance with an embodiment of the invention;

FIG. 5 is a top view of the blade of FIG. 4;

FIG. 6 is an illustrative sectional view showing a technique using a scalpel blade in accordance with the invention; and FIG. 7 is a sectional view illustrating the type of incision made in accordance with a technique of the invention.

DETAILED DESCRIPTION

In FIG. 1, there is shown an embodiment of scalpel 10 mounted in position with respect to a microscope 12 (shown schematically and only partly) and an eye 14 (shown in fragmentary sectional view) positioned for a sutureless incision. As shown in this view, the scalpel or surgical knife 10 includes a handle 18 and a bent blade portion 16 positioned to make an incision. The blade 16 has edges with double bevels.

In making an incision, a straight incision of the length necessary for the interocular lens that is to be inserted is made through the conjunctiva and one-half of the thickness of the schlera, one millimeter posterior to the clear cornea at twelve o'clock using a diamond blade. The inferior lip of the incision in undermined with a crescent knife until clear cornea is reached to form a short schleral tunnel.

The double-beveled surgical knife in accordance with the invention is then placed underneath the undermined inferior schleral lip and cutting movements from side to side are repeatedly made to advance it in the cleaved plane along one-half of the schlera until the point of the knife is seen through the clear cornea just within the corneal capillary ring.

As the knife is introduced under the schleral flap, its plane is more or less meridional, following the schleral plane. Using the point of the knife as a fulcrum, the plane of the blade is gradually rotated upwardly by lifting the end of the handle until the coaxial microscope light is reflected back through the microscope, causing a strong glare. In this position, the plane of the knife is 90 degrees to the microscope tube. This is done for an average-shaped cornea.

The eye 14 is held with a corneosclera forceps at six o'clock and rotated upwardly until the limbal plane is 90 degrees to the microscope tube. The plane of the blade 16 is rotated until it is past the glare, and then the blade 16 is moved to enter the anterior chamber.

With an embodiment of blade having reflective symbols along its length, the rotating may be done until the proper symbol is reached and then the incision into the anterior chamber may be made. This provides control of the angle in accordance with the intention of the surgeon.

In FIG. 2, there is shown a fragmentary perspective view of the blade 16 attached to a portion of the handle 18, which blade includes a pointed distal end 20 formed at the junction of edges 22 and 24. The edges 22 and 24 form an angle between them so that as the distance between the point of the blade increases, the distance between the edges increases.

The edges 22 and 24 are formed by beveled portions between a top surface 36 and a bottom surface 37 of the blade with the beveled, slanting planes 26 and 28 meeting to form the edge 22, and the corresponding beveled planes 30 and 31 (only plane 30 being shown in FIG. 2) meeting to form the edge 24. All four of the beveled surfaces meet at point 20 forming upwardly and backwardly slanting edges, such as the top edge 25 extending to the top surface 36. A similar edge extends to the bottom surface 37 formed by the beveled surface 28 and another surface which forms sharp edges 22 and 24. The surfaces of the beveled planes are equal in area, length, width and angle made with the center plane of the blade.

In some embodiments of scalpels, the top flat surface 36 is matted, knurled, roughened or colored at 38 to avoid strongly reflecting light as glare but contains upon it, in an order extending in a direction from the point 20 to the handle 18, polished reflective areas such as rectangular areas or lines 46 and 47, a diamond-shaped spot 44, a disk 42 and a ring 40. Any shapes can be used or a simple gradation of polished lines or the like which will indicate to the surgeon looking through the eye piece and seeing the glare, which symbol is reflecting light back into the eye piece.

As best shown in FIG. 1, as the blade 16 is tilted, different portions of the incident light are reflected at different angles from the surface so that different amounts of light flux or different patterns of light flux are reflected into the eye piece. Thus, as the angle of the blade 16 with respect to the incident light changes, corresponding ones of the different shaped polished units 40, 42, 44 46 and 47 are reflected outside of the eye piece. Thus, the physician, by moving the handle as he rotates it, can detect the angle of the blade by the polished symbols. Of course, light-absorbing coats can be used as the symbols and the rest of the background of the top surface 36 can be reflective.

In FIG. 3, there is shown a block diagram 50 of a technique using a scalpel in accordance with the invention to make a sutureless incision in microsurgical cataract removal operations, comprising: (1) the step 52 of aligning the eye and the microscope; (2) the step 54 of moving the microscope into position; (3) the step 58 of selecting the angle of the knife; (4) the step 56 of classifying the eye shape; and (5) the step 60 of making the incision.

Generally, the step 52 of aligning the eye and the microscope includes the step of aligning the patient so that when the microscope is positioned directly over the eye, the light transmitted through the microscope is reflected from the center of the eye back into the microscope tube. With the patient in this position, the axis of the light is perpendicular to the eye and the light would be reflected from a flat surface back into the microscope.

The step 54 of moving the microscope into position refers to moving the microscope to the location where the microsurgery is to take place while keeping the eye and the microscope in parallel planes. The patient remains stationary while the microscope is moved horizontally to the new location.

Under some circumstances, the shape of the eye may deviate from the average shape and require the angle of the incision to be adjusted to make an opening of the proper dimensions and in the proper location. For example, an eye that is narrower in diameter in the base plane and extends upwardly a greater distance for the same diameter than the average eye, may require a slightly upward angle to the cut rather than it being parallel, and an eye that has a wider diameter in the meridian plane as compared to its height may require a lower angle to obtain a valve which closes and is still of the proper shape.

For the average-shaped eye, the incision is parallel as described above, and a scalpel with a completely reflective surface is positioned with the light reflected from the knife back into the microscope tube indicating that it is parallel. If there are symbols, then a central symbol reflects its light back into the microscope.

For other shaped eyes, a different symbol would be reflected back into the microscope indicating to the surgeon that the knife is at the chosen angle. The bevel on the edge of the knife aids the surgeon in moving the knife into position since the tissue pressure as a cut is made is the same on both sides of the bevel instead of having greater pressure on the side away from the bevel as is the case when a single-beveled knife is used.

In FIG. 4, there is an elevational view of an unbent blade 16A similar to the blade 16 but without being bent at an angle to the handle 18 (FIG. 1) having the top surface 36 and the bottom surface 37 starting at the point 20 and widening to ears 39 and 41 (only 39 being shown in FIG. 4) and then sloping back to a stem portion 68. The thickness between the top and bottom surfaces 36 and 37 at the apex closest to the point 20 is between 0.004 and 9.008 of an inch and at the ears 37 and 41 where the edges of the blade no longer incline outwardly from each other and begin to decline inwardly is between 0.008 and 0.011 of an inch.

In FIG. 5, there is shown a plan view of the blade 16A with the tip 20 centered between the ears 39 and 41 and forming an angle at the tip 20 of 52 degrees, with the ears being spaced from each other a distance of between 0.122 and 0.128 of an inch and extending backwardly from the tip 20 a distance of between 0.125 of an inch and 0.165 of an inch.

In FIG. 6, there is shown a schematic view of a blade 16 making an incision in accordance with the technique of this invention in the limbal plane 66 of an eye 14 with its tip at 64 as would be done for a normally-shaped or average-shaped cornea. For a cornea which extends higher from the limbal plane and in which the limbal plane has a narrower ratio of the heighth of the cornea from the plane to the cornea to the diameter of the cornea, the blade 16 would be angled upwardly, and for an eye 14 in which the ratio of the heighth to the diameter is smaller, it would be angled downwardly. In FIG. 7, there is shown a plan view taken in an upward direction of an incision 69 showing that it is curvilinear to form a suitable valve flap and is within and adjacent to a capillary wall 62 when made in accordance with the invention.

From the above description, it can be understood that the technique of the scalpel in accordance with the invention has several advantages, such as: (1) the technique permits the surgeon to control the plane of the blade so as to provide reliable sutureless incisions repetitively; (2) the scalpel provides indications of whether it is level or not and at what angle it is being inserted; and (3) the double-beveled shape avoids inadvertent angulation of the blade during an incision because pressures are equalized on both sides of the blade.

Although a preferred embodiment of the invention has been described with some particularity, many modifications and variations of the invention are possible without deviating from the above teachings. Therefore, it is to be understood that, within the scope of the appended claims, the invention may be practiced other than as specifically described.

What is claimed is:

1. A scalpel having a blade with reflective and light-absorbing portions on its surface, whereby glare from the reflective portions of the blade indicate the angle of an incision; the blade including a plurality of portions that reflect light differently from other portions, wherein the angle can be identified by a characteristic of the reflected light.

2. A scalpel, comprising:
a blade with reflective and light-absorbing portions on its surface, whereby glare from the reflective portions of the blade indicate the angle of an incision;
said blade being a double-beveled thin blade for microsurgery; and
said blade including a plurality of portions that reflect light differently from other portions, wherein the angle can be identified by a characteristic of the reflected light.

3. A scalpel, comprising:
a blade with reflective and light-absorbing portions on its surface, whereby glare from the reflective portions of the blade indicate the angle of an incision;
said blade being a double-beveled thin blade for microsurgery; and
said blade including a plurality of portions spaced longitudinally along the blade of the scalpel that reflect light differently from other portions on the blade.

4. A combination of a scalpel and a microscope, comprising:
a scalpel having a double-beveled thin blade for microsurgery with reflective and light-absorbing portions on its surface whereby glare from the reflective portions of the blade indicate the angle of an incision;
said portions being spaced longitudinally along the blade of the scalpel;
said microscope having a source of light including means for irradiating light along a longitudinal axis and a tubular portion aligned with the longitudinal axis, whereby the light may be focused over the point where the incision is to be made; and
means for viewing light from the source of light reflected from the blade, wherein the angle of the scalpel with respect to the longitudinal axis can be determined during the incision by viewing the reflection of the light.

5. A method of making an incision comprising the steps of:
aligning a microscope tube with the cornea of an eye;
shining light from a light source on the eye;
aligning the microscope tube over the point where the incision is to be made;
inserting a scalpel, the blade of which is at least partly reflective of light from the light source; and
controlling the angle of the scalpel during the incision by viewing the reflection of the light.

6. A method in accordance with claim 5 in which the step of shining the light from the light source includes the step of shining the light through a tubular portion of the microscope.

7. A method in accordance with claim 5 in which the blade of the scalpel is maintained perpendicular to the axis of the microscope tube by maintaining the reflective glare within the portion of the microscope tube during the incision.

8. A method in accordance with claim 6 in which the angle of the blade with respect to the axis of the microscope tube is controlled so as to control the angle of the incision with respect to the cornea by maintaining a particular reflective portion of the scalpel formed by light incident at an angle to the blade within the microscope tube, whereby different indicia may indicate different angles of the blade.

9. A method in accordance with claim 5 in which the step of inserting a scalpel includes the step of inserting a scalpel, the blade of which includes at least one double beveled edge.

10. A method in accordance with claim 5 in which the step of inserting a scalpel includes the step of inserting a scalpel, the blade of which includes two double beveled edges tapering to a point.

11. A method in accordance with claim 5 in which the step of inserting a scalpel includes the steps of:
inserting a scalpel, the blade of which includes a plurality of portions that reflect light differently from other portions; and
controlling the angle of the scalpel during the incision by viewing the reflection in the microscope, wherein different reflections indicate different angles of the scalpel blade during the incision.

* * * * *